| (12) | United States Patent | (10) Patent No.: | US 7,564,939 B2 |
|---|---|---|---|
| | Morton et al. | (45) Date of Patent: | Jul. 21, 2009 |

(54) CONTROL MEANS FOR HEAT LOAD IN X-RAY SCANNING APPARATUS

(75) Inventors: Edward James Morton, Guildford (GB); Russell David Luggar, Dorking (GB); Paul De Antonis, Horsham (GB)

(73) Assignee: Rapiscan Systems, Inc., Hawthorne, CA (US)

( * ) Notice: Subject to any disclaimer, the term of this patent is extended or adjusted under 35 U.S.C. 154(b) by 0 days.

(21) Appl. No.: 10/554,656

(22) PCT Filed: Apr. 23, 2004

(86) PCT No.: PCT/GB2004/001729

§ 371 (c)(1),
(2), (4) Date: Mar. 29, 2007

(87) PCT Pub. No.: WO2004/097386

PCT Pub. Date: Nov. 11, 2004

(65) Prior Publication Data

US 2007/0172023 A1  Jul. 26, 2007

(30) Foreign Application Priority Data

Apr. 25, 2003  (GB) ................................. 0309387.9

(51) Int. Cl.
*A61B 6/00* (2006.01)
(52) U.S. Cl. .............................. 378/9; 378/57; 378/121
(58) Field of Classification Search ............... 378/4–20, 378/57, 119, 121, 134
See application file for complete search history.

(56) References Cited

U.S. PATENT DOCUMENTS 2,952,790 A  9/1960  Steen

| 3,239,706 | A | 3/1966 | Farrell et al. |
|---|---|---|---|
| 3,768,645 | A | 10/1973 | Conway et al. |
| 4,057,725 | A | 11/1977 | Wagner |
| 4,105,922 | A | 8/1978 | Lambert et al. |
| 4,228,353 | A | 10/1980 | Johnson |

(Continued)

FOREIGN PATENT DOCUMENTS

DE  2729353  1/1979

(Continued)

OTHER PUBLICATIONS

PCT Search Report, Aug. 10, 2004, Morton, Edward James et al Search Report PCT/GB2004/001729.

(Continued)

*Primary Examiner*—Courtney Thomas
(74) *Attorney, Agent, or Firm*—Patentmetrix

(57) ABSTRACT

An X-ray scanning apparatus comprises a number of multi-focus X-ray tubes (25) spaced around an axis X and arranged to emit X-rays through an object on the axis which are detected by sensors (52). Each tube (25) can emit X-rays from a plurality of source positions. In each scanning cycle, in which each of the source positions in each of the tubes is used once, the ordering of the positions used is arranged so as to minimize the thermal load on the tubes (25). This is achieved by ensuring that each source position is non-adjacent to the previously active one and the next active one.

16 Claims, 3 Drawing Sheets

U.S. PATENT DOCUMENTS

| | | |
|---|---|---|
| 4,259,721 A | 3/1981 | Kuznia |
| 4,266,425 A | 5/1981 | Allport |
| 4,274,005 A | 6/1981 | Yamamura et al. |
| 4,340,816 A | 7/1982 | Schott |
| 4,352,021 A | 9/1982 | Boyd et al. |
| 4,468,802 A | 8/1984 | Friedel |
| 4,672,649 A | 6/1987 | Rutt |
| 4,675,890 A | 6/1987 | Plessis et al. |
| RE32,961 E | 6/1989 | Wagner |
| 4,866,745 A | 9/1989 | Akai |
| 4,868,856 A | 9/1989 | Frith et al. |
| 4,887,604 A | 12/1989 | Shefer et al. |
| 5,033,106 A | 7/1991 | Kita |
| 5,247,556 A | 9/1993 | Eckert et al. |
| 5,259,014 A | 11/1993 | Brettschneider |
| 5,272,627 A | 12/1993 | Maschhoff et al. |
| 5,313,511 A | 5/1994 | Annis et al. |
| 5,367,552 A | 11/1994 | Peschmann |
| 5,467,377 A | 11/1995 | Dawson |
| 5,511,104 A | 4/1996 | Mueller et al. |
| 5,604,778 A | 2/1997 | Polacin et al. |
| 5,633,907 A | 5/1997 | Gravelle et al. |
| 5,689,541 A | 11/1997 | Schardt |
| 5,841,831 A | 11/1998 | Hell et al. |
| 5,859,891 A | 1/1999 | Hibbard |
| 5,966,422 A | 10/1999 | Dafni et al. |
| 5,974,111 A | 10/1999 | Krug et al. |
| 5,987,097 A | 11/1999 | Salasoo |
| 6,018,562 A | 1/2000 | Willson |
| 6,122,343 A | 9/2000 | Pidcock |
| 6,181,765 B1 | 1/2001 | Sribar et al. |
| 6,183,139 B1 | 2/2001 | Solomon et al. |
| 6,218,943 B1 | 4/2001 | Ellenbogen |
| 6,236,709 B1 | 5/2001 | Perry et al. |
| 6,269,142 B1 | 7/2001 | Smith |
| 6,324,249 B1 | 11/2001 | Fazzio |
| 6,546,072 B1 | 4/2003 | Chalmers |
| 6,735,271 B1 | 5/2004 | Rand et al. |
| 7,233,644 B1 * | 6/2007 | Bendahan et al. ............. 378/57 |
| 2001/0022346 A1 | 9/2001 | Katagami et al. |
| 2002/0031202 A1 | 3/2002 | Callerame et al. |
| 2002/0094064 A1 | 7/2002 | Zhou et al. |
| 2002/0176531 A1 | 11/2002 | McClelland et al. |
| 2003/0031352 A1 | 2/2003 | Nelson et al. |
| 2004/0120454 A1 | 6/2004 | Ellenbogen et al. |
| 2004/0252807 A1 | 12/2004 | Skatter et al. |
| 2004/0258305 A1 | 12/2004 | Burnham et al. |
| 2005/0031075 A1 | 2/2005 | Hopkins et al. |
| 2005/0053189 A1 | 3/2005 | Gohno et al. |
| 2005/0105682 A1 | 5/2005 | Heumann et al. |
| 2005/0111610 A1 | 5/2005 | De Man et al. |
| 2005/0157925 A1 | 7/2005 | Lorenz |

FOREIGN PATENT DOCUMENTS

| | | |
|---|---|---|
| EP | 0 432 568 | 6/1991 |
| EP | 0 531 993 | 3/1993 |
| EP | 0 584 871 | 3/1994 |
| EP | 0 924 742 | 6/1999 |
| EP | 0 930 046 | 7/1999 |
| EP | 1 277 439 | 1/2003 |
| EP | 1374776 | 1/2004 |
| FR | 2328280 | 5/1977 |
| GB | 1497396 | 1/1978 |
| GB | 1526041 | 9/1978 |
| GB | 2 015 245 | 9/1979 |
| GB | 2089109 | 6/1982 |
| GB | 2 212 903 | 8/1989 |
| JP | 2004 079128 | 3/1992 |
| JP | 2001 176408 | 6/2001 |
| WO | WO 95/28715 | 10/1995 |
| WO | WO 99/60387 | 11/1999 |
| WO | WO 03/051201 | 6/2003 |

OTHER PUBLICATIONS

US 5,987,079, 11/1999, Scott et al. (withdrawn)

* cited by examiner

CONTROL MEANS FOR HEAT LOAD IN X-RAY SCANNING APPARATUS

CROSS-REFERENCE TO RELATED APPLICATIONS

The present application is a national stage application of PCT/GB2004/001729, filed on Apr. 23, 2004. The present application further relies on Great Britain Patent Application Number 0309387.9, filed on Apr. 25, 2003, for priority.

BACKGROUND OF THE INVENTION

The present invention relates to X-ray scanning in which X-rays are directed through an object from a number of positions around the object and the X-rays transmitted through the object are detected and used to build up an image of the object. This type of scanning is referred to as computed tomography (CT) scanning.

One method of CT scanning involves rotating an X-ray source around the object so that it directs X-rays through the object in different directions. Another method, for example as disclosed in U.S. Pat. No. 4,274,005, involves positioning a number of X-ray sources around the object and then operating the sources in turn so that the active source position scans round the object.

As the use of X-ray scanners, for example in security applications, increases, there is an increasing demand for scanners which operate quickly and which have a long lifetime.

SUMMARY OF THE INVENTION

Accordingly the present invention provides an X-ray imaging apparatus comprising X-ray production means arranged to produce X-rays from a plurality of source positions spaced around an object location and spaced from each other by a source spacing, a plurality of X-ray sensors arranged to be spaced around the object position so as to detect X-rays emitted from the source positions and passing through the object position, and control means arranged to control the order in which the source positions are active such that the average smallest displacement between an active source position in one emission period and an active source position in the subsequent period is greater than the source spacing.

This increase in average spacing between successively active source positions helps to spread the thermal load in the X-ray source.

Preferably said average smallest displacement is at least twice the source spacing. This can most easily be achieved by ensuring that the control means is arranged such that no active source position in any one emission period is adjacent a source position active in the next emission period.

The control means may arranged so that in each emission period only one source position is active.

Alternatively the control means may arrange such that in each emission period a plurality of source positions are active simultaneously. This can reduce the scanning time and increase the scanning rate.

Where the source positions are each arranged to produce X-rays which will be detected by a corresponding group of sensors, the control means is preferably arranged such that in each emission period, there is no overlap between the groups of sensors for said plurality of source positions. This ensures that the detected X-rays from each of the simultaneously active sources can be distinguished.

Preferably in each emission period at least half of the sensors are arranged to receive X-rays from the active source positions. More preferably in each emission period substantially all of the sensors are arranged to receive X-rays from the active source positions.

Preferably the apparatus comprises a plurality of X-ray tubes each providing a plurality of said source positions.

In this case the control means is preferably arranged such that in each emission period the active source position is in a different tube from the active source position in the previous emission period.

Conveniently only one source position is active in each emission period and the active source positions are provided in each of the tubes in turn.

Preferably, within each tube, the order in which the source positions are active is arranged such that in each emission period the active source position is non-adjacent to the source position active in the previous emission period.

BRIEF DESCRIPTION OF THE DRAWINGS

Preferred embodiments of the present invention will now be described by way of example only with reference to the accompanying drawings in which.

DETAILED DESCRIPTION OF THE DRAWINGS

Figure 1:
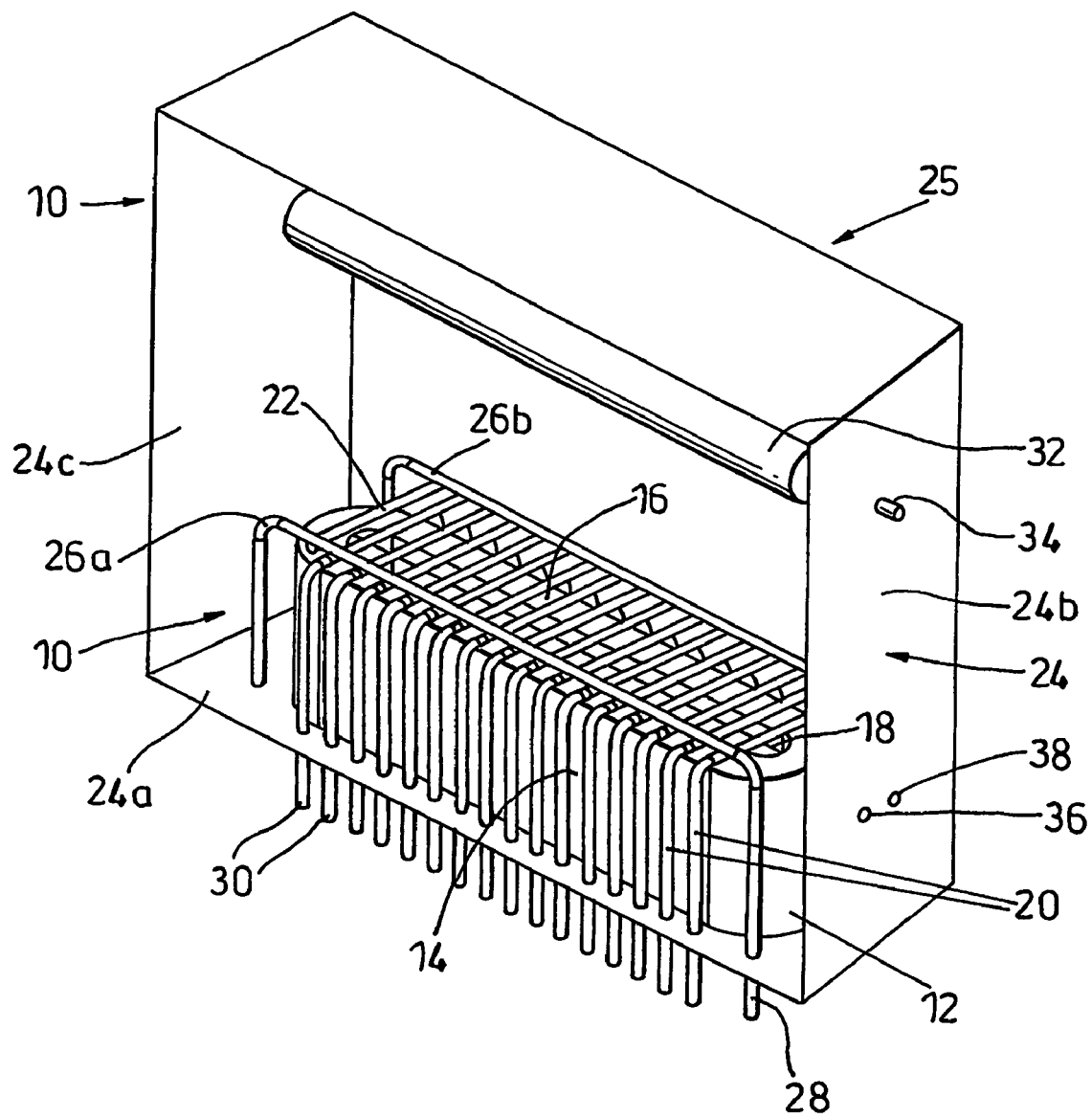
FIG. 1 shows an X-ray emitter suitable for use with the invention.

Referring to FIG. 1, a multi-focus X-ray tube 10 comprises a ceramic former 12 and an emitter element 18 extending along between the sides 14, 16 of the former. A number of grid elements in the form of grid wires 20 are supported on the former 12 and extend over the gap between its two sides 14, 16 perpendicular to the emitter element 18, but in a plane which is parallel to it. A number of focusing elements in the form of focusing wires 22 are supported in another plane on the opposite side of the grid wires to the emitter element. The focusing wires 22 are parallel to the grid wires 20 and spaced apart from each other with the same spacing as the grid wires, each focusing wire 22 being aligned with a respective one of the grid wires 20.

The source 10 is enclosed in a housing 24 of an emitter unit 25 with the former 12 being supported on the base 24a of the housing. The focusing wires 22 are supported on two support rails 26a, 26b which extend parallel to the emitter element 18, and are spaced from the former 12, the support rails being mounted on the base 24a of the housing. The support rails 26a, 26b are electrically conducting so that all of the focusing wires 22 are electrically connected together. One of the support rails 26a is connected to a connector 28 which projects through the base 24a of the housing to provide an electrical connection for the focusing wires 22. Each of the grid wires 20 extends down one side 16 of the former and is connected to a respective electrical connector 30 which provide separate electrical connections for each of the grid wires 20.

An anode 32 is supported between the side walls 24b, 24c of the housing. The anode extends parallel to the emitter element 18. The grid and focusing wires 20, 22 therefore extend between the emitter element 18 and the anode 32. An electrical connector 34 to the anode extends through the side wall 24b of the housing.

The emitter element 18 is supported in the ends of the former and is heated by means of an electric current supplied to it via further connectors 36, 38 in the housing.

In order to produce a beam of electrons from one position, a pair of adjacent grid wires 20 can be connected to an extracting potential which is positive with respect to the element 18 while the remaining grid wires are connected to a blocking potential which is negative with respect to the element 18. By selecting which pair of wires 20 is used to extract electrons, the position of the beam of electrons can be chosen. As the X-rays will be emitted from the anode 32 at a point where the electrons strike it, the position of the X-ray source can also be chosen by choosing the extracting pair of grid wires. The focusing elements 22 are all kept at a positive potential with respect to the grid wires 20 so that electrons extracted between any pair of the grid wires will also pass between, and be focused by, a corresponding pair of focusing elements 22.

Figure 2:
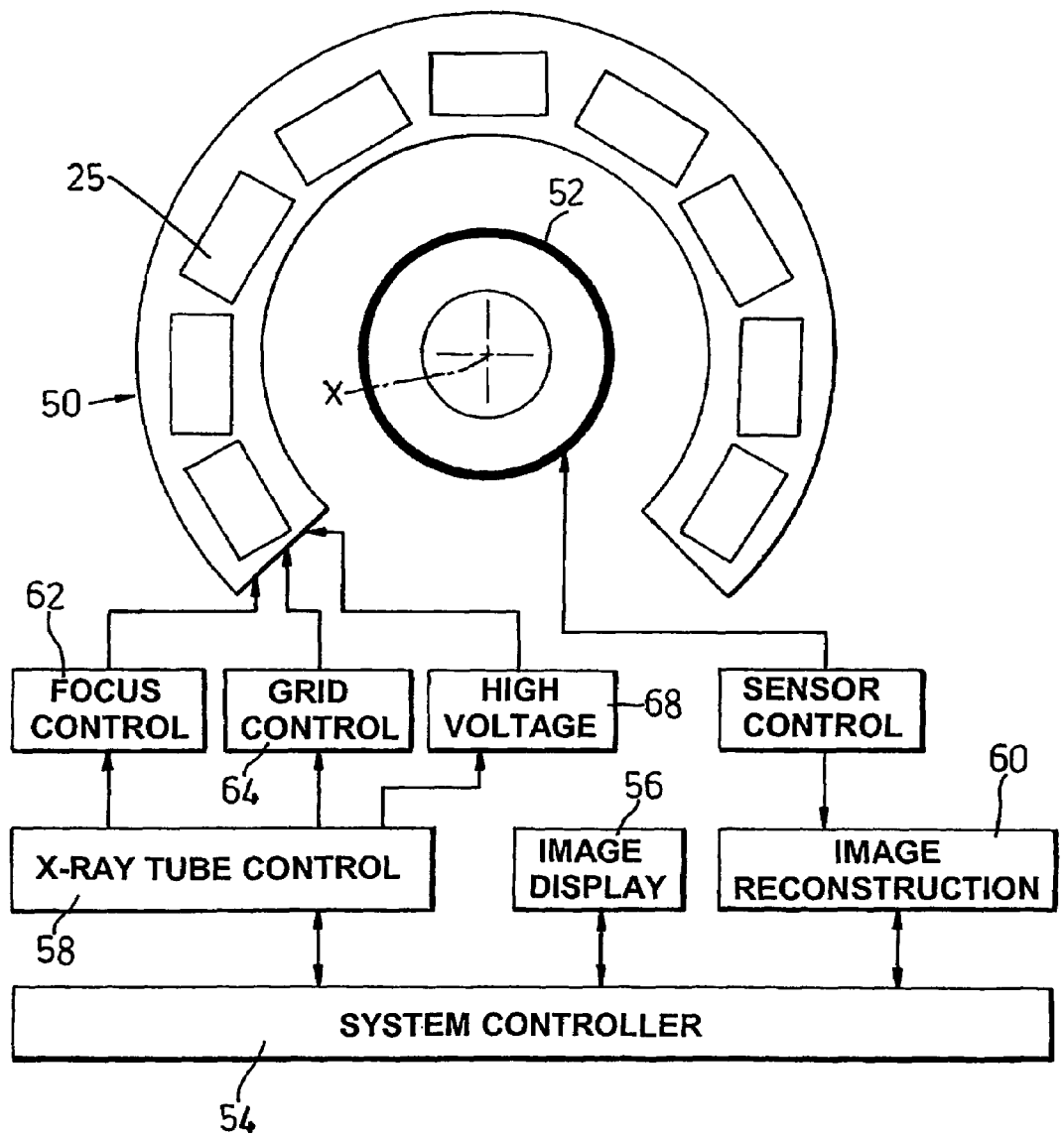
FIG. 2 is a diagram of an X-ray imaging system according to the invention including a number of emitter units as shown in FIG. 1.

Referring to FIG. 2, an X-ray scanner 50 is set up in a conventional geometry and comprises an array of emitter units 25 arranged in an arc around a central scanner axis X, and orientated so as to emit X-rays towards the scanner axis X. A ring of sensors 52 is placed inside the emitters, directed inwards towards the scanner axis. The sensors 52 and emitter units 25 are offset from each other along the axis X so that X-rays emitted from the emitter units pass by the sensors nearest to them, through the object, and are detected by a number of sensors furthest from them. The number of sensors 52 that will detect X-rays from each source depends on the width of the fan of X-rays that is emitted from each source position in the tubes 25. The scanner is controlled by a control system which operates a number of functions represented by functional blocks in FIG. 5. A system control block 54 controls, and receives data from, an image display unit 56, an X-ray tube control block 58 and an image reconstruction block 60. The X-ray tube control block 58 controls a focus control block 62 which controls the potentials of the focus wires 22 in each of the emitter units 25, a grid control block 64 which controls the potential of the individual grid wires 20 in each emitter unit 25, and a high voltage supply 68 which provides the power to the anode 32 of each of the emitter blocks and the power to the emitter elements 18. The image reconstruction block 60 controls and receives data from a sensor control block 70 which in turn controls and receives data from the sensors 52.

In operation, an object to be scanned is passed along the axis X, and X-ray beams are directed through the object from the X-ray tubes 25. In each scanning cycle each source position in each tube 25 is used once, the scanning cycle being repeated as the object moves along the axis X. Each source position produces a fan of X-rays which after passing through the object are detected by a number of the sensors 52. However, the order in which the tubes and the positions within the tubes are used is controlled as will now be described.

The order of X-ray emission from the source positions in the tubes 25 is chosen so as to minimize the thermal load on the X-ray tube. This is achieved by ordering the emissions so that each source position is non-adjacent to, and therefore spaced from, the previous one and the subsequent one. This ordering applies both to the source positions within each tube 25, and also to the tubes themselves. Therefore each source position is in a different tube to the previous one and the next one. In fact the best distribution of thermal load is achieved if the source position cycles through all of the tubes, using one position from each tube, and then cycles through the tubes again using a different source position within each tube. The cycling is then repeated until all of the source positions in all of the tubes have been used once. This completes one scanning cycle which can then be repeated.

Within each tube the source positions are taken in an order which spreads the thermal load within the tube. This is achieved by ordering the source positions so that the distance between each source position and the next one in that tube, and the previous one in that tube, are both maximized. Firstly, therefore, if the number of source positions per tube allows it, each source position in the tube should be non-adjacent to the next and previous ones in that tube. Then, depending on the number of source positions, the ordering is chosen so as to distribute the thermal load as much as possible.

Figure 3:
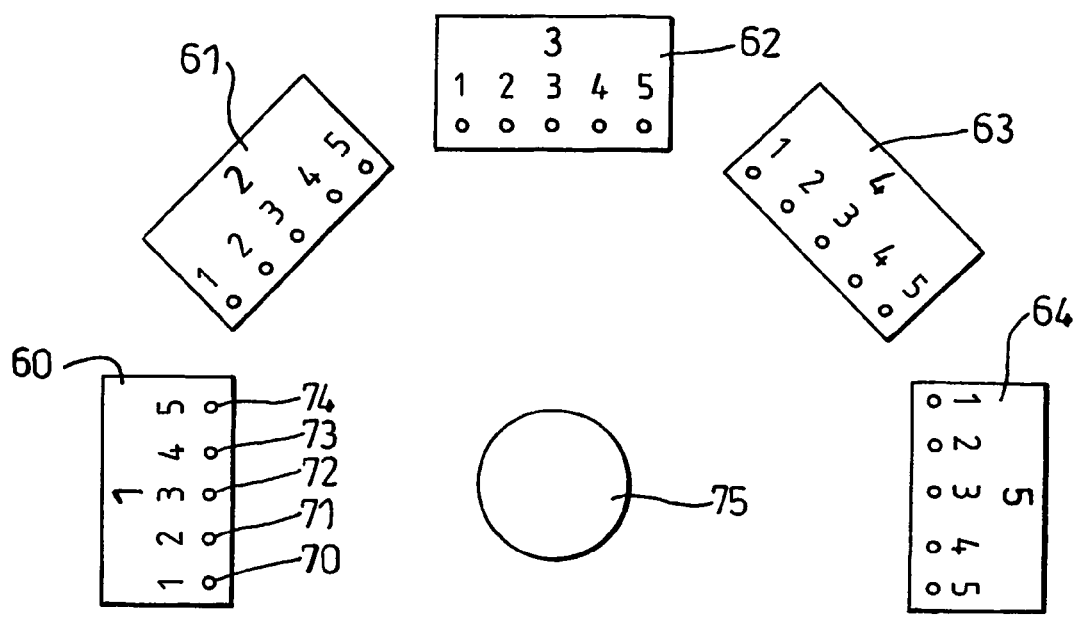
FIG. 3 is a diagram of the layout of an X-ray imaging system according to a second embodiment of the invention.

For example, if as in a second embodiment of the invention shown in FIG. 3, there are five X-ray tubes 60, 61, 62, 63, 64 numbered in the order in which they are positioned 1, 2, 3, 4 and 5, and each one can produce X-rays from 5 source positions 70, 71, 72, 73, also numbered in order along the tube 60 as 1, 2, 3, 4 and 5, then best ordering for the source positions within each tube is 1, 3, 5, 2, 4. The same sequence is also used for ordering the tubes so as to maximize the angular separation between successive emissions. This produces an emission ordering as follows, where the source positions are numbered in order round the object 75 starting at the left hand end of the tube 60 at the left end of the row and counting to the right hand end of the tube 64 at the right end of the row.

| Tube | Source Position in Tube | Overall Source position |
|---|---|---|
| 1 | 1 | 1 |
| 3 | 1 | 11 |
| 5 | 1 | 21 |
| 2 | 1 | 6 |
| 4 | 1 | 16 |
| 1 | 3 | 3 |
| 3 | 3 | 13 |
| 5 | 3 | 23 |
| 2 | 3 | 8 |
| 4 | 3 | 18 |
| 1 | 5 | 5 |
| 3 | 5 | 15 |
| 5 | 5 | 25 |
| 2 | 5 | 10 |
| 4 | 5 | 20 |
| 1 | 2 | 2 |
| 3 | 2 | 12 |
| 5 | 2 | 22 |
| 2 | 2 | 7 |
| 4 | 2 | 17 |
| 1 | 4 | 4 |
| 3 | 4 | 14 |
| 5 | 4 | 24 |
| 2 | 4 | 9 |
| 4 | 4 | 19 |

The same ordering could also be used with, for example, 25 source positions in a single tube which is shaped around the object 75.

It will be appreciated that, for X-ray tubes with less than 5 source positions it is not possible to avoid using adjacent positions in subsequent emissions. However, for tubes with 5 or more source positions, this can be avoided.

Figure 4:
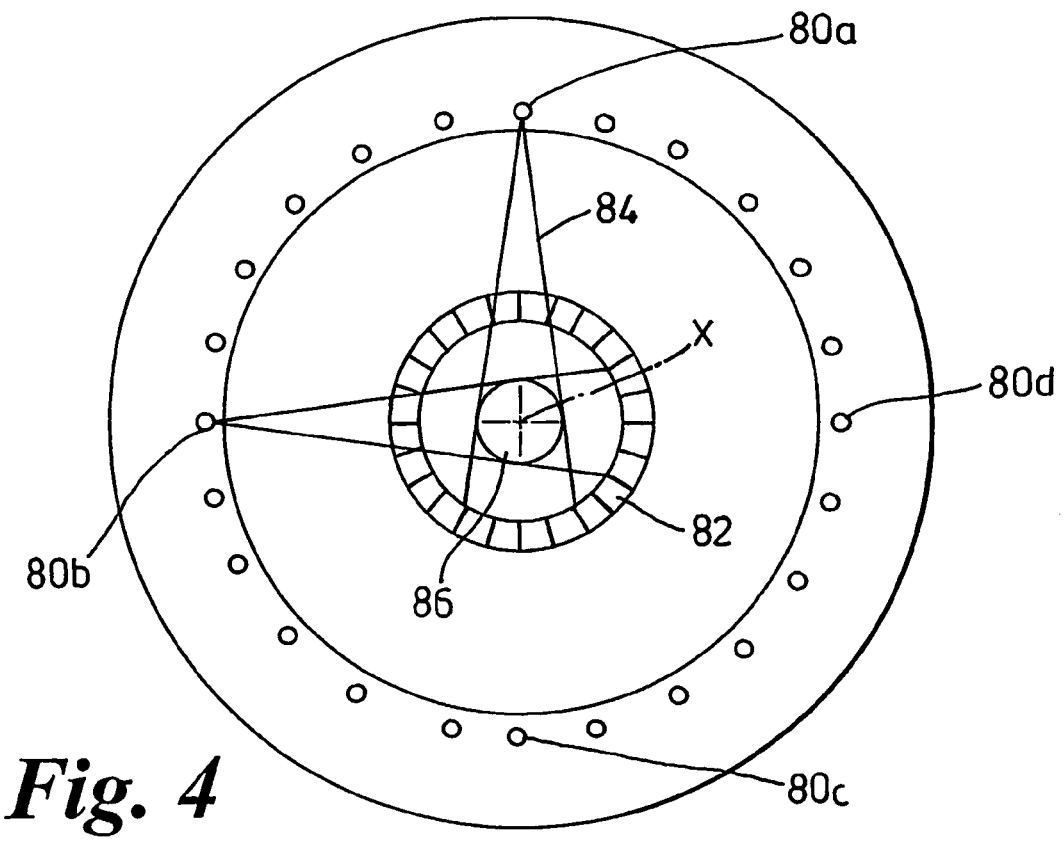
FIG. 4 is a diagram of the layout of an X-ray imaging system according to a third embodiment of the invention.

Referring to FIG. 4, in a third embodiment of the invention a plurality of X-ray sources 80 are spaced around an axis X, with a plurality of sensors 82 axially offset from the sources 80 as in the first embodiment. When one of the sources 80a emits an X-ray beam 84 this diverges, passes through the object 86 and reaches a number of the sensors 82. The number of sensors 82 which will detect X-rays from each of the sources depends on the width of the beam of X-rays, which is a known quantity for any give system, and can be quantified in terms of a half-angle. This is the angle between the centre of the beam and the edge of the beam.

When the sensors 82 which are needed to detect X-rays from each of the source positions 80 are known, source positions can be selected which can emit simultaneously, provided that they do not require any common detectors. For example if there are 24 source positions 80 and 24 sensors 82 and each source position requires 5 sensors, then four of the sensors 80a, 80b, 80c, 80d, spaced around the object at 90° intervals can be used simultaneously.

In practice the number of source positions and sensors is likely to be higher than this. To satisfy the Nyquist sampling theorem, it is necessary to match the number of source positions $N_\phi$ to the number of sensors $N_s$ of width d that are required to cover the linear dimension of the object $N_s d$. This leads to the result $$N_\phi = \pi N_s / 2.$$

For example an image where $N_s=64$ will require $N_\phi=100$ sampling points to satisfy the Nyquist sampling criterion.

It will be appreciated that the ordering of the emission positions can be varied in a large number of ways for any given number of emission positions, and that the optimum ordering will also vary depending on the number of emission positions and the number of X-ray tubes.

The invention claimed is:

1. An X-ray imaging apparatus comprising:
   a plurality of X-ray tubes comprising a first X-ray tube for producing X-rays from a plurality of sources and a second X-ray tube for producing X-rays from a plurality of sources wherein the first X-ray tube and second X-ray tube are adjacent each other and spaced from each other by a spacing;
   a plurality of X-ray sensors to detect X-rays emitted from the plurality of X-ray tubes and passed through an object; and
   control means for controlling an order in which the X-ray tubes are active such that a displacement between an active X-ray tube in one emission period and an active X-ray tube in a period immediately after the emission period is greater than the spacing.

2. The imaging apparatus of claim 1 wherein said displacement is at least twice the spacing.

3. The imaging apparatus of claim 1 wherein an active X-ray tube in said emission period is not adjacent a X-ray tube position that is active in the period immediately after the emission period.

4. The imaging apparatus of claim 1 wherein only one X-ray tube is active in each emission period.

5. The imaging apparatus of claim 1 wherein a plurality of X-ray tube are active simultaneously in each emission period.

6. The imaging apparatus of claim 5 wherein each of the X-ray tubes produces X-rays for detection by at least one corresponding group of sensors, wherein during each emission period, the group of sensors are not overlapping.

7. The imaging apparatus of claim 6 wherein in each emission period at least half of the sensors are arranged to receive X-rays from the active X-ray tubes.

8. The imaging apparatus of claim 7 wherein in each emission period substantially all of the sensors are arranged to receive X-rays from the active X-ray tubes.

9. An X-ray imaging apparatus comprising:
   a plurality of X-ray tubes, each of said X-ray tubes comprising a plurality of source positions, including a first source position and a second source position, wherein the first source position and the second source position are adjacent each other and spaced from each other by a source spacing;
   a plurality of X-ray sensors to detect X-rays emitted from the plurality of X-ray tubes and passed through an object; and
   a controller for controlling an order in which the X-ray source positions are active such that a displacement between an active source position in one emission period and an active source position in a period immediately after the emission period is greater than the source spacing.

10. The imaging apparatus of claim 9 wherein said displacement is at least twice the source spacing.

11. The imaging apparatus of claim 9 wherein an active source position in the emission period is not adjacent a source position that is active in the period immediately after the emission period.

12. The imaging apparatus of claim 9 wherein only one source position in an X-ray tube is active in each emission period.

13. The imaging apparatus of claim 12 wherein a plurality of X-ray tubes are active simultaneously in each emission period.

14. The imaging apparatus of claim 9 wherein, in each emission period, more than one source position is active and each of said active source positions is located in a different X-ray tube.

15. The imaging apparatus of claim 9 wherein only one source position in each X-ray tube is active in each emission period and each X-ray tube is active in a sequential order.

16. The imaging apparatus of claim 9 wherein, within each X-ray tube, an order in which source positions are active is arranged such that, in each emission period, an active source position is not adjacent to a source position that was active in a period immediately preceding the emission period.

* * * * *